(12) United States Patent
Weese et al.

(10) Patent No.: US 9,367,904 B2
(45) Date of Patent: Jun. 14, 2016

(54) SPATIAL-TEMPORAL WARPING OF DIFFERENT PRE-CAPTURED MEDICAL IMAGES

(75) Inventors: Jurgen Weese, Aachen (DE); Jorg Bredno, San Francisco, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1007 days.

(21) Appl. No.: 12/596,847

(22) PCT Filed: Apr. 18, 2008

(86) PCT No.: PCT/IB2008/051490
§ 371 (c)(1),
(2), (4) Date: Oct. 21, 2009

(87) PCT Pub. No.: WO2008/129484
PCT Pub. Date: Oct. 30, 2008

(65) Prior Publication Data
US 2010/0128991 A1  May 27, 2010

(30) Foreign Application Priority Data

Apr. 23, 2007 (EP) .................................. 07106738

(51) Int. Cl.
*G06Q 50/22* (2012.01)
*G06T 5/50* (2006.01)
*A61B 6/00* (2006.01)
*G06Q 50/24* (2012.01)

(52) U.S. Cl.
CPC . *G06T 5/50* (2013.01); *A61B 6/481* (2013.01); *A61B 6/504* (2013.01); *G06T 2207/10116* (2013.01); *G06T 2207/30048* (2013.01); *G06T 2207/30101* (2013.01)

(58) Field of Classification Search
CPC ....... G06Q 50/22; G06Q 50/24; G06Q 40/08; G06Q 10/10; G06F 19/322
USPC .......................................................... 705/2
See application file for complete search history.

(56) References Cited

U.S. PATENT DOCUMENTS 5,273,040 A * 12/1993 Apicella et al. ............... 600/410
5,647,360 A *  7/1997 Bani-Hashemi .......... G06T 5/50
                                                    382/130
6,154,518 A   11/2000 Gupta
8,036,730 B1* 10/2011 Damadian et al. ............ 600/410

FOREIGN PATENT DOCUMENTS

EP        0840253 A2    5/1998
WO     2005039253 A1    4/2005

OTHER PUBLICATIONS

Cox et al: "Automatic Registration of Temporal Image Pairs for Digital Subtraction Angiography"; Image Processing, SPIE vol. 2167, 1994, pp. 188-199.

(Continued)

*Primary Examiner* — Tran Nguyen

(57) ABSTRACT

It is described a method for medical image comparison purposes, comprising the step of generating a first global image or mask with increased similarity to a second global image, wherein the first global image comprises at least partially a composition of different pre-captured images of a patient; wherein the pre-captured images are captured at different times.

9 Claims, 3 Drawing Sheets

(56) References Cited

OTHER PUBLICATIONS

Ro et al: "Computed Masks in Coronary Subtraction Imaging"; IEEE Transaction on Medical Imaging, vol. 6, No. 4, Dec. 1987, pp. 297-300.

Meijering et al: Retrospective Motion Correction in Digital Subtraction Angiography: A Review; IEEE Transactions on Medical Imaging, vol. 18, No. 1, Jan. 1999, pp. 2-21.

Van Tran et al: "Flexible Mask Subtraction for Digital Angiography"; IEEE Transactions on Medical Imaging, vol. 11, No. 3, Sep. 1992, pp. 407-415.

Beier et al: "Advanced Subtraction Angiography: Mask Selection and Image Registration"; Computers in Cardiology, 1994, pp. 105-108.

Meijering, E.: "Image Enhancement in Digital X-Ray Angiography"; PhD Thesis, University of Utrecht, Jul. 2000, pp. 47,50,51,53, 57.

\* cited by examiner

SPATIAL-TEMPORAL WARPING OF DIFFERENT PRE-CAPTURED MEDICAL IMAGES

FIELD OF INVENTION

The present invention relates generally to the field of medical digital imaging. More particular, the present invention relates to the field of digital subtraction angiography (DSA). Even more particular, the invention relates to cardiac subtraction angiography (CSA). More precisely, the present invention relates to a method for medical image comparison purposes in the field of X-ray imaging, further to an image processing device and a software program applicable for DSA or CSA and other medical fields.

ART BACKGROUND

DSA is an established method for diagnostic viewing and quantitative assessment of neurovascular and peripheral interventional X-ray. Particularly, interventional imaging of heart and coronaries is an important field of application but a cardiac DSA revealing the contrast agent in the moving coronaries is not yet available for diagnostic viewing with sufficient quality or to enable subsequent quantitative coronary angiography (QCA).

In state of research and technology, for subtraction of an image in form of a diagnostic angiogram, a pre-captured image is selected sometimes referred as the mask image or mask that shows the heart in the same phase of the cardiac cycle and without contrast agent. The mask is then spatially deformed (warped) to compensate for residual motion to result in a subtraction image with as little subjective visual artifacts as possible.

A deformation vector field that results in best-possible matching of mask and angiogram is created and applied to the mask prior to subtraction.

The EP 0 840 253 relates generally to a method for X-ray imaging and, more particularly, to DSA for imaging vasculature. According to EP 0 840 253 a method for generating a DSA image from mask image data and opacified image data is described. The mask image is referred to as the X-ray image taken before injecting a contrast agent into the blood vessels. The opacified image is referred to as the X-ray image taken after injecting the contrast agent.

For patients with coronary heart disease, i.e. the target patient group of coronary angiography, irregularities in shape and dynamics of the heart beat—especially after injection of contrast agent—are observed. In consequence, available masks are not always sufficient to capture the contraction status of the heart in an angiogram frame and, therefore, provide a high-quality mask input. Even when single DSA frames are of high subjective visual quality, a discontinuity or wrap-around artifact is visible in a sequence of multiple heart beats whenever the end of the mask frame acquisition is reached and an earlier frame has to be selected for subtraction.

Thus, a high-quality coronary subtraction angiograph is important to allow for improved diagnostic viewing and to enable subsequent quantitative coronary angiography QCA.

There may be a need for an effective and a reliable method, which may be provided within a compact configuration and which may generate medical images, preferably DSA images, more accurately. Such accurate images should preferably have minimum artifacts due, e.g. to motion of the patient or its organs, and should be corrected for any misregistration changes from one part of the image to another part of the image.

SUMMARY OF THE INVENTION

This need may be met by a method for medical image comparison purposes, comprising the step of generating a first global image with increased similarity or with maximum correlation to a second global image, wherein the first global image comprises at least partially a composition of different pre-captured images of a patient and wherein the pre-captured images are captured at different times.

Therefore a local spatial-temporal warping of the pre-captured images is possible to compensate for irregularities between the first global image and the second global image. Thus, the invention implements a new time dimension, because additional to the warping or displacement of image coordinates, pre-captured images of different times are selectable to get the aforesaid increased similarity between the first and the second global image. According to the fields of DSA and CSA, the pre-captured images may be defined as X-ray images taken before injecting a contrast agent into the blood vessels of the patient. A pre-captured image or "pre-bolus" image may be defined as the mask or mask image. Further, the second global image may be referred to as an X-ray image taken after injecting the contrast agent or briefly the "contrast image".

According to an embodiment of the invention as set forth in claim 2, the first global image is fragmented into a plurality of image regions or frames. This regions may have rectangular or every other even irregular shape. The size of such a region may set to just one pixel. At least one of the image regions make use of a matching region of at least one first pre-captured image, and an adjacent region make use of a matching region of at least one second pre-captured image.

In a preferred embodiment, the first global image is generated such, that a composition of regions of pre-captured images is selected which reaches an increased similarity to the second global image compared to other selections. This composition constitutes the first global image. Thus the selection of a single pre-captured image region as it is known from state of the art, e.g. EP 0 840 253, is replaced with a selection of multiple pre-captured image regions of different pre-captured images.

The matching process may start in one embodiment of the invention with the selection of interesting image regions or points in a multitude of the pre-captured images. Points or regions of high local intensity variation may considered interesting because they are easy to match. Only the interesting regions/points are matched with their corresponding regions or points in the second global image, in CSA or DSA the "contrast image".

Thus, the interesting regions of the second global image have multiple matching regions of different pre-captured images. Further, for each of the interesting regions of the second global image at least one matching region of at least one pre-captured image is selected with a increased similarity to the respective regions of the second global image compared to the matching regions of the remaining pre-captured images. The selected regions constitutes the first global image. Hence, the first global image is a composition of different pre-captured images, precisely regions there from, as described above.

Because of rotation or translation of the patient body or its organs even the regions of the first and second image may be rotated or translated with respect to each other. Further the regions could be interpolated with data of regions of remaining pre-captured images, which involves the possibility of applying interpolation-, correlation-, and later warping processes in a third dimension, which is in fact a kind of time dimension, because the pre-captured images are captured at different times.

If the inventive method is used in the field of DSA or CSA, the local spatial-temporal warping of pre-captured images compensates irregularities in heart beat and the change of the shape of heart beat after contrast injection between the first and the second global image.

One aspect of the invention is to determine a three-dimensional deformation vector field with a local temporal shift (local change of mask frame) as the additional above dimension. Changing dynamics and shape after the injection of contrast agent are reflected in the selection of regions of different pre-captured images (masks) for different regions of the second global image.

Thus, according to a second embodiment of the invention as claimed in claim 2, the first global image is fragmented into a plurality of image regions wherein at least one of the image regions makes use of a matching region of at least one first pre-captured image and an adjacent image region makes use of a matching region of at least one second pre-captured image.

According to a further embodiment of the invention as set forth in claim 3, the method further comprises the steps of generating a locally-adaptive and/or temporal adaptive image transform and applying the transform to the first global image to generate a warp image.

According to a further embodiment of the invention as set forth in claim 4, the method of claim 3, further comprises the step of applying, particularly subtracting the warp image values from the second global image.

According to a further embodiment of the invention as set forth in claim 5, the pre-captured images are X-ray images.

According to a further embodiment of the invention as set forth in claim 6, the method is used for generating a digital subtraction angiography image.

According to a further embodiment of the invention as set forth in claim 7, the method further comprises the steps of selecting of a sequence of pre-captured images of a complete heart beat cycle, pre-processing of the matching regions of the selected pre-captured images, generating of a deformation vector field of the matching regions of the last and the first matching pre-captured image in the heart beat cycle and applying the deformation vector field to all matching regions of the remaining pre-captured images.

According to a further embodiment of the invention as set forth in claim 8, an image processing device is claimed. The image device comprises a memory for storing images of a patient and an image processor for registering a plurality of pre-captured images. The image processor is adapted to perform the following operation: generating a first global image, wherein the first global image comprises a composition of different pre-captured images, computing of a deformation vector field for at least two of the pre-captured images and applying the deformation vector field to a first or second global image of the patient such that the similarity between the first global image and the second global image increases.

According to a further embodiment of the invention as set forth in claim 9, a software program for registering a plurality of pre-captured images is claimed. The software program causes a processor to o perform the following operation: generating a first global image, wherein the first global image comprises a composition of different pre-captured images, computing of a deformation vector field for at least two of the pre-captured images and applying the deformation vector field to the first or a second global image of the patient such that the similarity between the first global image and the second global image increases.

"Applying the deformation vector field" is defined in a further embodiment of the invention as a gradually application of said field, such that the "latest" pre-captured image is deformed completely down to the "first" pre-captured image which is not deformed at all. The images in-between these two images are deformed less each time.

With the gradually application of the vector field to the pre-captured images the discontinuity artifact of mask wrap-around may eliminated such that a stable heart beat with no wrap-around discontinuity artifacts is available as a mask input, preferably for cardiac DSA.

According to a further embodiment of the invention as set forth in claim 10, a spatial deformation vector field is computed preferably between the last and the first mask of a selected heart cycle. These two frames show the heart in the same contraction state but of course, these frames are not identical. The residual deformation vector field between these frames can eliminate the visible flicker artefact between the two frames. In order to avoid the artefact completely, it is proposed to apply this deformation vector field linearly interpolated over the heart cycle such that the discontinuities is eliminated by small, gradual deformations. One selected full heart beat in the mask frame sequence is pre-processed. The matching of the last and the first frame in this selected heart beat results in a deformation vector field that can be applied (in temporal interpolation) to all mask frames such that a stable heart beat with no wrap-around discontinuity artifacts is visible.

In the field of current cardiac DSA two major modifications and extensions are proposed to reduce the amount of subtraction artifacts:

The selection of a single pre-captured image or mask frame is replaced with a selection of multiple pre-captured regions or mask frames for each region in the image that is used to determine a deformation vector field for later warping. In different regions of the image, different mask frames can better capture the local state of heart contraction, especially in the presence of irregularities due to pathology and contrast injection.

Further, it has to be noted that certain embodiments of the invention have been described with reference to a method, whereas other embodiments of the invention have been described with reference to an image processing device and to a software program. However, a person skilled in the art will gather from the above and the following description that, unless otherwise notified, in addition to any combination of features belonging to one category of claims also any combination of features as described in different claims is possible and considered to be disclosed within this application.

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

DETAILED DESCRIPTION

Figure 1:
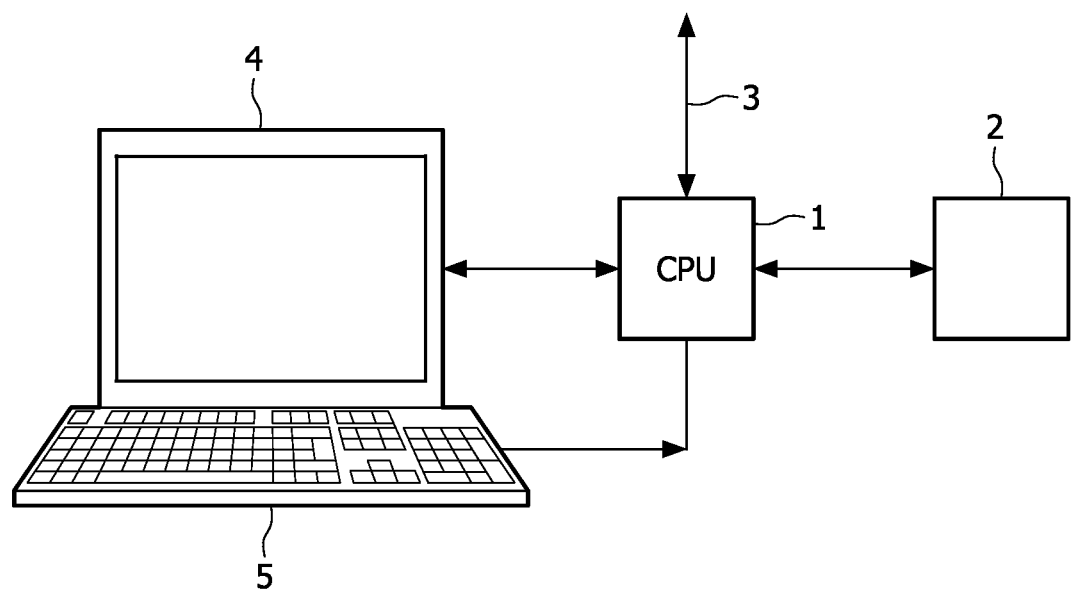
FIG. 1 shows a schematic representation of an image processing device according to an exemplary embodiment of the present invention, adapted to execute a method according to an exemplary embodiment of the present invention.

FIG. 1 depicts an exemplary embodiment of an image processing device according to the present invention, for executing an exemplary embodiment of a method in accordance with the present invention. The image processing device depicted in FIG. 1 comprises a central processing unit (CPU) or image processor 1 to perform warping operations connected to a memory 2 for storing images of a patient, e.g. data of pre-captured images. The image processor 1 may be connected to a plurality of input/output network 3 or diagnosis devices such as an interventional X-ray imaging device. The image processor 1 is furthermore connected to a display device 4 (for example, a computer monitor) for displaying information or images computed or adapted in the image processor 1. An operator may interact with the image processor 1 via a keyboard 5 and/or other input/output devices which are not depicted in FIG. 1.

In spite of the fact that the method is described in the following with reference to medical applications, in particular applications in DSA, it should be noted that the present invention can be applied to any multi-dimensional data sets or images required to be warped. For example, the present invention may be applied to quality testing of medical images, where actual images are compared to former images. Also, the method may be applied for medical follow-up studies, for example, for monitoring changes to a patients heart over a certain period of time.

Figure 2:
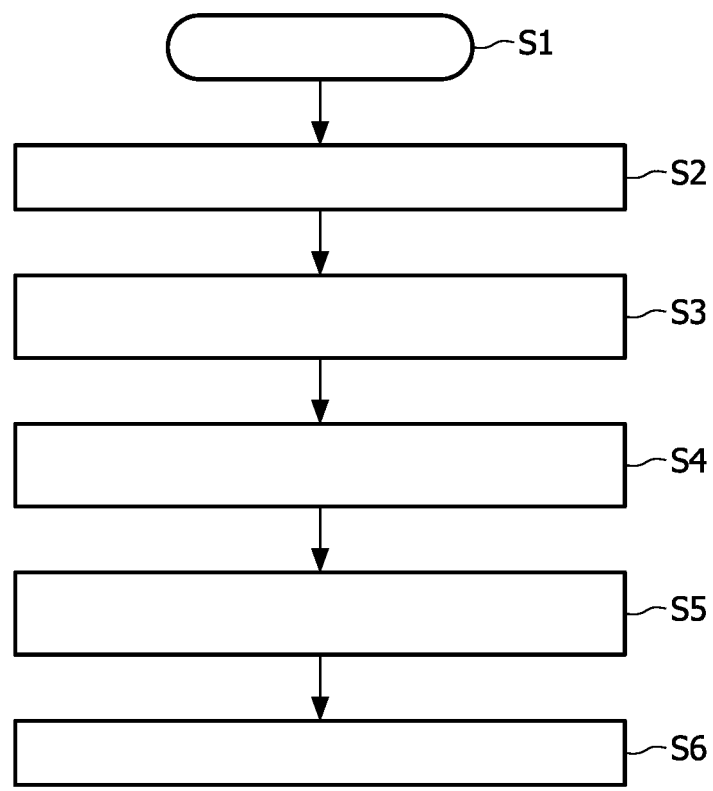
FIG. 2 shows a simplified flow-chart of an exemplary embodiment of a method according to the present invention.

FIG. 2 shows a flow-chart of an exemplary embodiment of a method for registering a first and a second image according to the present invention.

As may be taken from FIG. 2, after the start in step S1, interesting regions in each of the stored pre-captured images are identified in step 2. Then, in the subsequent step S3, the locally corresponding matching regions of a second global image are determined. Then, in the subsequent step S4, the regions of pre-captured images with increased similarity to the corresponding regions of the second global image are selected. All selected regions define a first global image. Regions with a maximum correlation to the respective regions of the second global image may be preferred in the selection step. The values of a spatial-temporal vector field are subsequently varied in the subsequent step S5 in a warping process such that the similarity between the first global image and the second global image is maximized. Specifically the spatial-temporal displacement of the selected regions is varied by interpolation. In the subsequent step S6, the deformation vector field is applied to the first global image to obtain a warp image. In a further step, the warped image data is subtracted from the corresponding second global image data to obtain the final DSA image as shown exemplary in FIG. 4 and FIG. 6.

Figure 3:
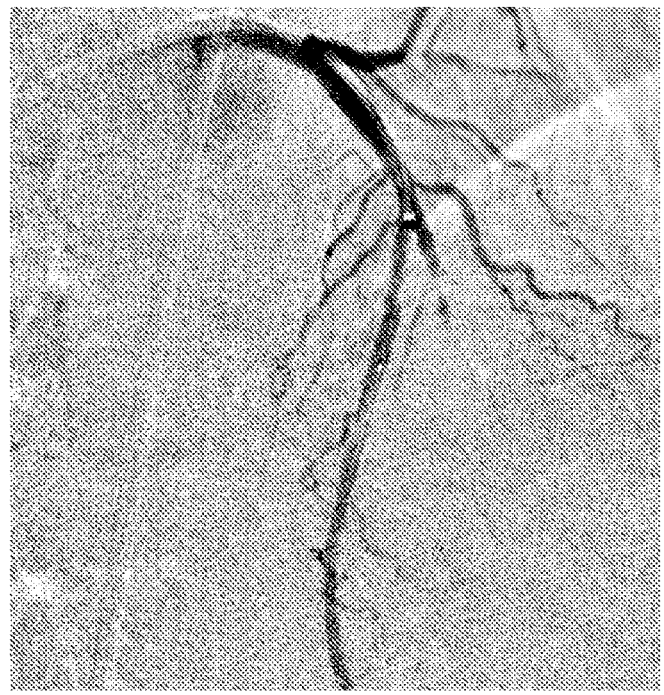
FIG. 3 shows a DSA image obtained from a single pre-captured warped image and a second image.
Figure 4:
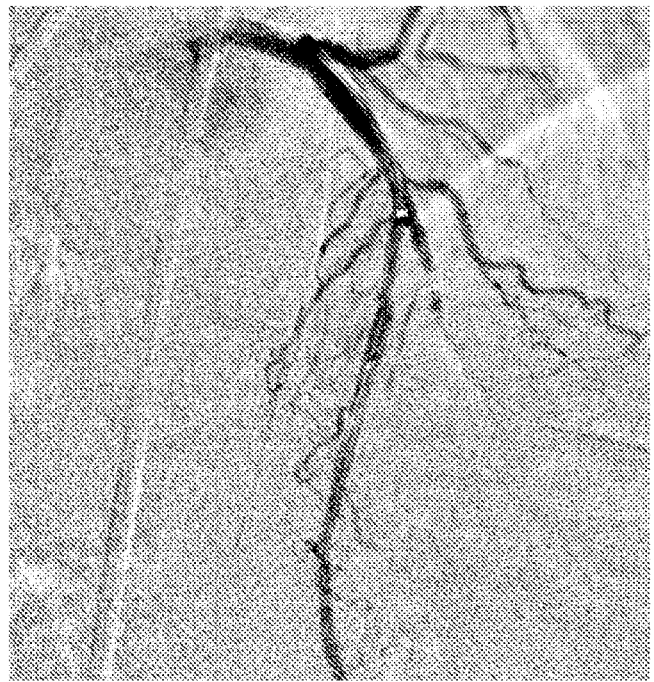
FIG. 4 shows the DSA image obtained from a multitude of temporally warped pre-captured images and the second image.
Figure 5:
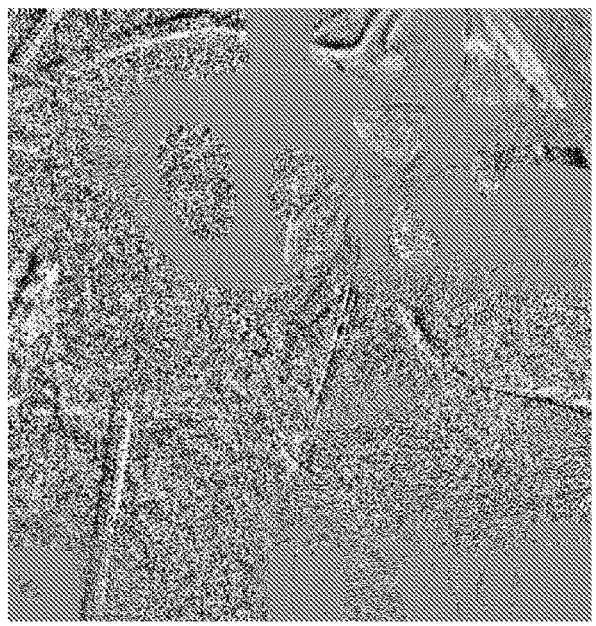
FIG. 5 shows the difference of the pre-captured warped images used in FIG. 1 and FIG. 2.
Figure 6:
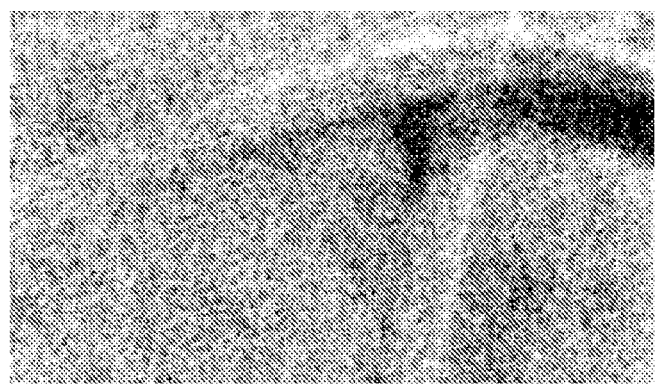
FIG. 6 shows a scaled up section of the upper left corner of FIG. 3.
Figure 7:
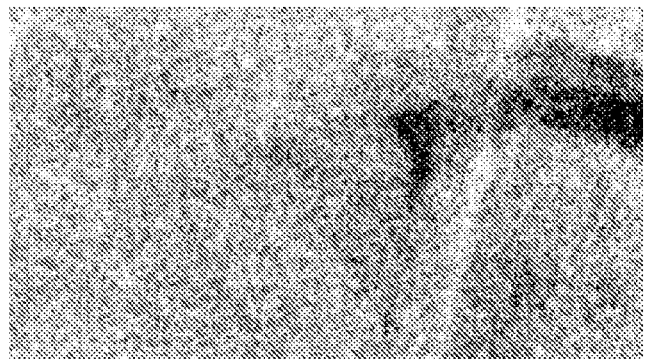
FIG. 7 shows a scaled up section of the upper left corner of FIG. 4.

FIG. 3 shows a DSA image obtained from a single pre-captured warped image and a second image and FIG. 4 shows the DSA image obtained from a multitude of temporally warped pre-captured images and the second image. FIG. 5 shows the difference of the pre-captured warped images used in FIG. 1 and FIG. 2. FIG. 6 shows a scaled up section of the upper left corner of FIG. 3 and FIG. 7 shows a scaled up section of the upper left corner of FIG. 4.

According to FIG. 4, one pre-captured image (mask) is selected from a list of candidate pre-captured images that allows for the best match to the angiogram prior to subtraction. A local spatial-temporal warping of pre-captured images compensates irregularities in heart beat and the change of the shape of heart beat after contrast injection.

Competing methods are known to determine a deformation vector field that results in the best possible match of angiogram frame and deformed pre-captured image. Currently, all of these methods are planar and the essential enhancement of this invention is to determine a deformation vector field with a local temporal shift (local change of mask frame) as additional dimension. In consequence, for a heartbeat that has changed in dynamics and shape after the injection of contrast agent, this is reflected in the selection of different masks for different regions of the image. In consequence, a spatial-temporal warping replaces the current planar warping in mask deformation and synthesis. The effect of this method in comparison to single best mask selection is shown in FIGS. 3 to 7. FIG. 7 shows strongly reduced artifacts from a non-perfectly matched catheter. In comparison, FIG. 6 shows an DSA image with strong side shadows of the catheter. The image of FIG. 6 was obtained by state-of-the-art warping methods with one single pre-captured image.

Mask acquisitions usually cover one heart cycle whereas an angiogram sequence contains multiple heart beats. In consequence, a wrap-around artifact (flicker) is visible in the subtracted sequence at the end of each heart mask cycle. This artifact is already reduced when above spatial-temporal mask warping is applied as the wrap-around artifact then appears distributed over multiple angiogram frames. The claimed method may eliminate this artifact.

It should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

LIST OF REFERENCE SIGNS

1 image processor
2 memory
3 input/output network
4 display device
5 keyboard

The invention claimed is:

1. A method for reducing artifacts in medical imaging comprising the steps of:
   storing in a memory of an image device having an image processor a set of pre-captured images of a patient taken before and after injection of a contrast agent, wherein the pre-captured images are obtained at different times from an earliest pre-captured image to a latest pre-captured image;
   selecting anatomical regions of interest in the pre-captured images taken before the injection;
   selecting locally corresponding matching regions in the pre-captured images taken after the injection, wherein at least one of the regions of interest corresponds to a first matching region of at least one first pre-captured image, and an adjacent region of interest corresponds to a second matching region of at least one second pre-captured image;

comparing the selected regions of interest in the pre-captured images taken before the injection to the locally corresponding matching regions in the pre-captured images taken after the injection, thereby creating a spatial-temporal vector field of their similarity;

warping the spatial-temporal vector field by non-planar interpolation, wherein the warping is gradually applied to convert the latest pre-captured image into the earliest pre-captured image which is not warped at all, thereby obtaining a warp image having maximized similarity and reduced artefacts that were distributed over multiple pre-captured images and wherein the spatial-temporal displacement of the selected regions is varied by interpolation;

applying the warp image to any pre-captured image to produce a resulting image, wherein the applying the warp image to any pre-captured image is subtracting the warp image from the pre-captured image; and displaying the resulting image on a display.

2. The method according to claim 1, wherein the pre-captured images are X-ray images.

3. The method according to claim 1, wherein the method is used for generating a digital subtraction angiography image.

4. The method according to claim 1, further comprising the steps of:

selecting a sequence of pre-captured images of a complete heart beat cycle;

pre-processing of the matching regions of the selected pre-captured images;

generating a deformation vector field of the matching regions of the last and the first matching pre-captured image in the heart beat cycle;

applying the deformation vector field to all matching regions of the remaining pre-captured images.

5. The method of claim 1, further comprising the steps of selecting regions of the pre-captured images of one selected full heart beat cycle of a patient;

computing a spatial deformation vector field between a last and a first pre-captured image region of the selected heart cycle;

applying the deformation vector field linearly interpolated over the heart cycle such that discontinuities are eliminated by gradual deformations.

6. The method of claim 1, wherein the warping of the spatial-temporal vector field is done by interpolation or by correlation, or is locally-adaptive or temporally-adaptive.

7. An image processing device for reducing artifacts in medical imaging, comprising:

a memory for storing images of a patient; a display for displaying images;

an image processor for registering a plurality of pre-captured images, wherein the image processor is configured to perform the following steps:

receiving and storing in memory pre-captured images of a patient taken before and after injection of a contrast agent, wherein the pre-captured images are obtained at different times from an earliest pre-captured image to a latest pre-captured image;

selecting anatomical regions of interest in the pre-captured images taken before the injection;

selecting locally corresponding matching regions in the pre-captured images taken after the injection, wherein at least one of the regions of interest corresponds to a first matching region of at least one first pre-captured image, and an adjacent region of interest corresponds to a second matching region of at least one second pre-captured image;

comparing the selected regions of interest in the pre-captured images taken before the injection to the locally corresponding matching regions, thereby creating a spatial-temporal vector field of their similarity;

warping the spatial-temporal vector field by non-planar interpolation, wherein the warping is gradually applied to convert the latest pre-captured image into the earliest pre-captured image which is not warped at all, thereby obtaining a warp image having maximized similarity and reduced artefacts that were distributed over multiple pre-captured images and wherein the spatial-temporal displacement of the selected regions is varied by interpolation;

applying the warp image to any pre-captured image to produce a resulting image, wherein the applying the warp image to any pre-captured image is subtracting the warp image from the pre-captured image; and displaying the resulting image on a display.

8. The device of claim 7, wherein the image processor is configured to receive and store in memory pre-captured X-ray images.

9. The device of claim 7, wherein the image processor is configured to generate a digital subtraction angiography image.

* * * * *